US005199952A

United States Patent [19]

Marshall, Sr. et al.

[11] Patent Number: 5,199,952

[45] Date of Patent: Apr. 6, 1993

[54] BIRD INJECTION SYSTEM

[75] Inventors: William M. Marshall, Sr., Salem; Gordon J. Lancaster, Jr., Bent Mountain; Richard L. Booker, Salem, all of Va.

[73] Assignee: Morf, Inc., Salem, Va.

[21] Appl. No.: 682,606

[22] Filed: Apr. 9, 1991

[51] Int. Cl.$^5$ .......... A61M 5/20

[52] U.S. Cl. .......... 604/156; 604/198

[58] Field of Search .......... 604/115, 117, 131, 136–139, 604/144, 156, 157, 192, 198, 263

[56] References Cited

U.S. PATENT DOCUMENTS

| | | | |
|---|---|---|---|
| 3,314,428 | 4/1967 | Johnson et al. | 604/192 |
| 3,656,472 | 4/1972 | Moura | 604/136 |
| 3,964,481 | 6/1976 | Gourlandt | 604/156 X |
| 4,026,288 | 5/1977 | Costa et al. | 604/157 |
| 4,108,176 | 8/1978 | Walden | 604/147 X |
| 4,276,879 | 7/1981 | Yiournas | 604/156 X |
| 4,515,590 | 5/1985 | Daniel | 604/156 |
| 4,642,099 | 2/1987 | Phillips et al. | 604/198 |
| 4,676,781 | 6/1987 | Phillips et al. | 604/136 |
| 4,758,227 | 7/1988 | Lancaster et al. | 604/144 |

FOREIGN PATENT DOCUMENTS

| | | | |
|---|---|---|---|
| 1362060 | 4/1964 | France | 604/136 |

*Primary Examiner*—John D. Yasko
*Assistant Examiner*—Anthony Gutowski
*Attorney, Agent, or Firm*—John F. C. Glenn

[57] ABSTRACT

Bird's neck vaccine injector has fixed tubular guard around an injection needle. The guard is adapted to have a bird's neck pulled against it by pulling loose skin from the neck, and to have the pulled skin drawn over the projecting end of the guard and pressed against the guard so that the needle may be advanced to pierce the skin next to the projecting end of the guard and then inject vaccine into the cavity resulting from pull on the skin.

2 Claims, 4 Drawing Sheets

BIRD INJECTION SYSTEM

BACKGROUND OF THE INVENTION

It is conventional to inject subcutaneous oil-base vaccine into an adult chicken by pulling away the relatively loose flesh around the neck and using an injection needle to pierce the pulled-away skin and inject the vaccine into the cavity between the pulled-away skin and the underlying solid tissue. Hand-held injectors have been used for this purpose, but serious problems have been encountered. One is the difficulty in controlling the operation of the needle due to its discharge end being close to the operator's fingers but concealed by the bird's feathers. The result that sometimes the operator does not realize that the needle has not pierced the bird's skin before activating ejection from the needle. This causes the bird not to receive the intended injection and also wastes expensive vaccine. Another serious problem is risk of injury if one of the operator's fingers gets in the path of the needle advancing toward the bird's skin. If the vaccine enters a finger, amputation may be necessary, depending on the amount and kind of vaccine injected. Even when the bird's skin is pierced successfully, there still remains the risk of also causing the needle to stab into the neck, which usually injures the bird.

SUMMARY OF THE INVENTION

The present invention provides means for avoiding these difficulties through use of a guard around an injection needle which protects fingers while the needle is retracted, provides a predetermined position for anchoring a part of the bird's skin being grasped to draw the skin away from the neck, and guides the needle to pierce the part of the skin stretched closely across the end of the guard. Stop means limit the advance of the needle beyond the guard so that it will pierce the part of the skin across the guard but not touch anything other than fatty tissue accumulated in the cavity between the bird's skin and the underlying solid tissue. The lower part of the projecting end of the guard provides a place to position the top of the bird's neck so that the needle will advance to its intended position for injection.

The needle preferably advances through the guard so that its sharp end emerges from the lower part of the projecting end of the guard, which bears against the top of the chicken's neck. This guides the projecting end of the needle to enter the cavity between the bird's drawn skin and the underlying solid tissue where the cavity has the most room to receive the needle. In order to position the needle to so emerge from the guard, it is preferable to mount the needle so that it advances in a line which slopes downwardly relative to the central axis of the guard, which is preferably in the form of a cylindrical tube.

By so controlling the entry of the needle into the cavity formed by the bird's drawn skin, it is possible to have a single operator inject a chicken with improved speed, safety, and efficiency. The principles of the invention are applicable to other birds and animals of suitable nature for the purpose.

Other advantages, objects and details of the invention will become apparent as the following disclosure proceeds.

BRIEF DESCRIPTION OF THE DRAWINGS

Present preferred embodiments of the invention are shown, for purposes of illustration only, in the accompanying drawings, in which.

DETAILED DESCRIPTION OF PRESENT PREFERRED EMBODIMENTS OF THE INVENTION

Figure 1:
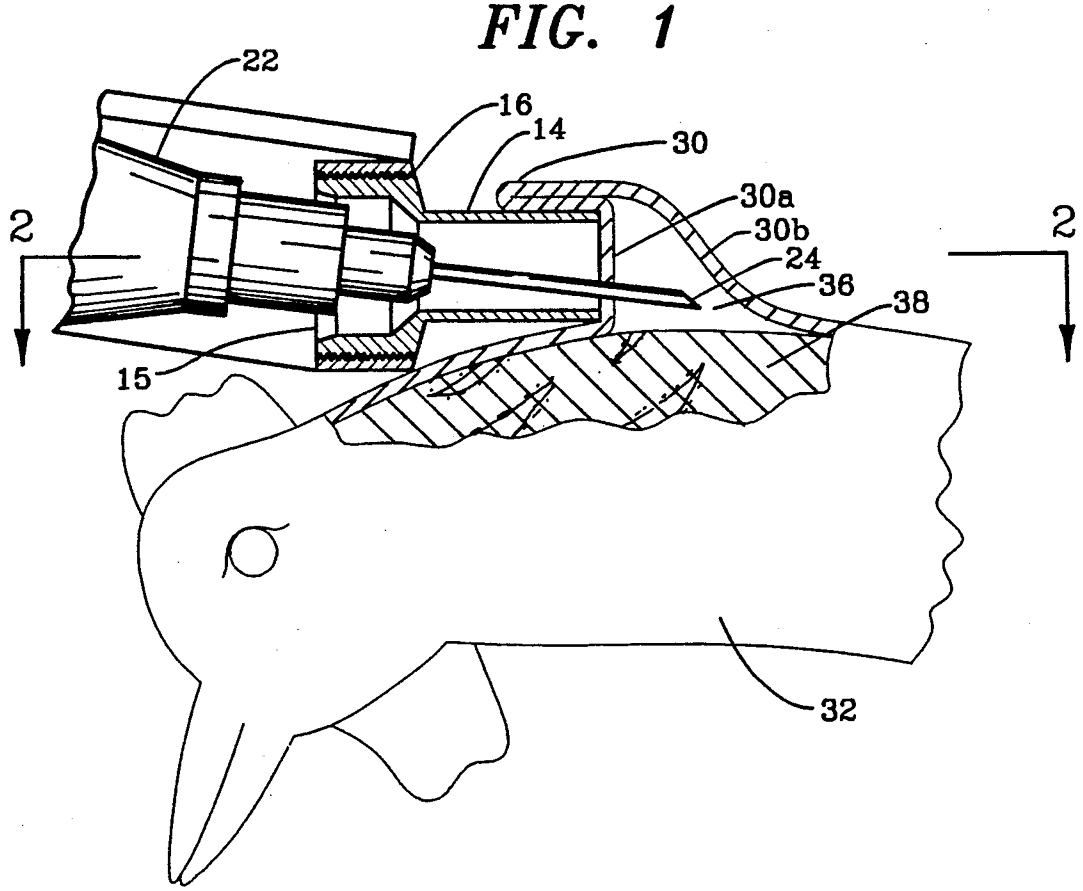
FIG. 1 shows a partially sectioned view of the head and neck of a chicken (omitting the feathers) receiving a subcutaneous injection from a needle, guard and vaccine pump in accordance with the invention.
Figure 2:
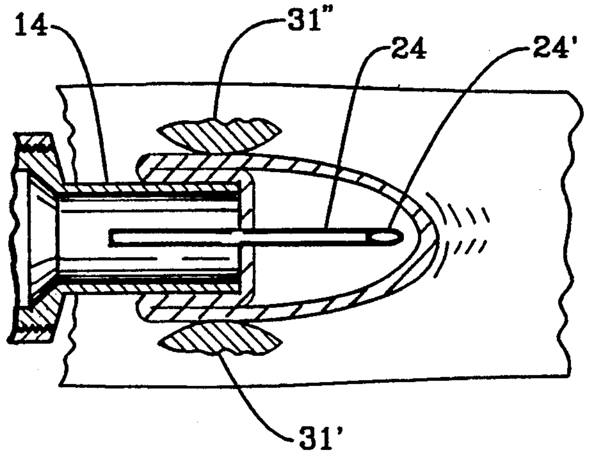
FIG. 2 shows a broken-away section on the line II—II shown in FIG. 1 (adding part of the operator's thumb and forefinger)
Figure 3:
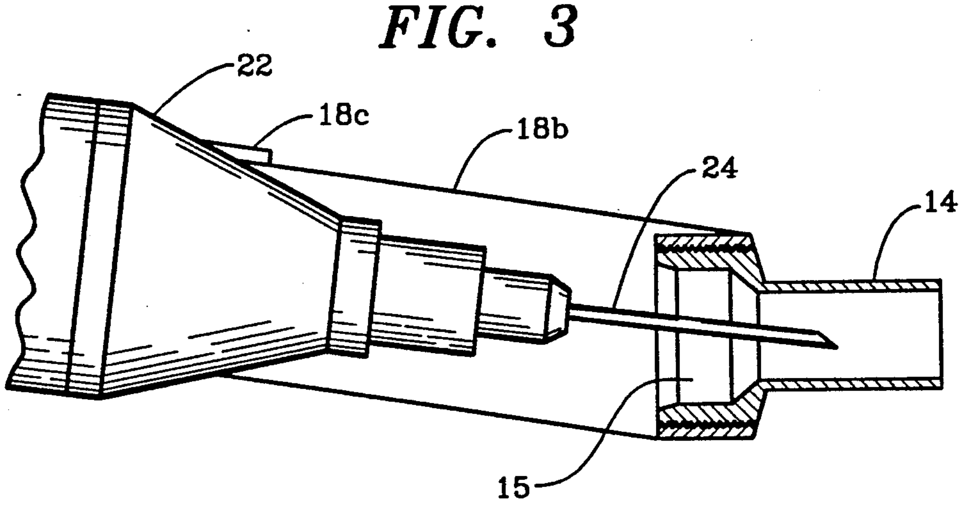
FIG. 3 shows a partially sectioned view of the needle, guard and pump shown in FIG. 1, in reduced scale and showing the needle and pump in retracted position.
Figure 4:
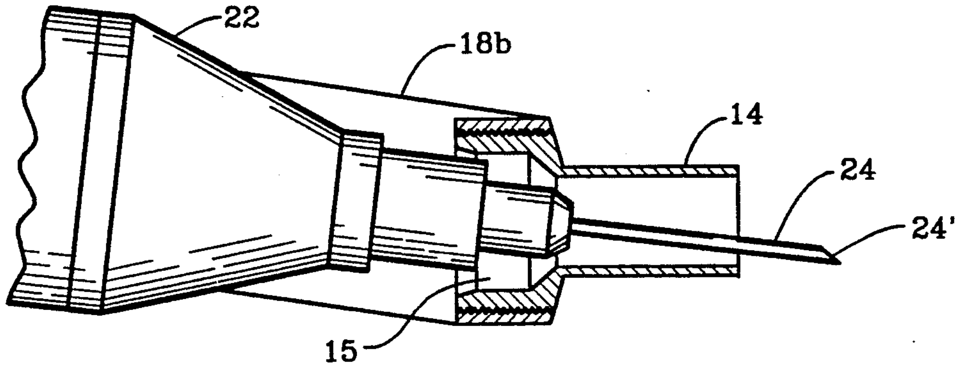
FIG. 4 corresponds to FIG. 3, but shows the needle and pump advanced to position for injection.
Figure 5:
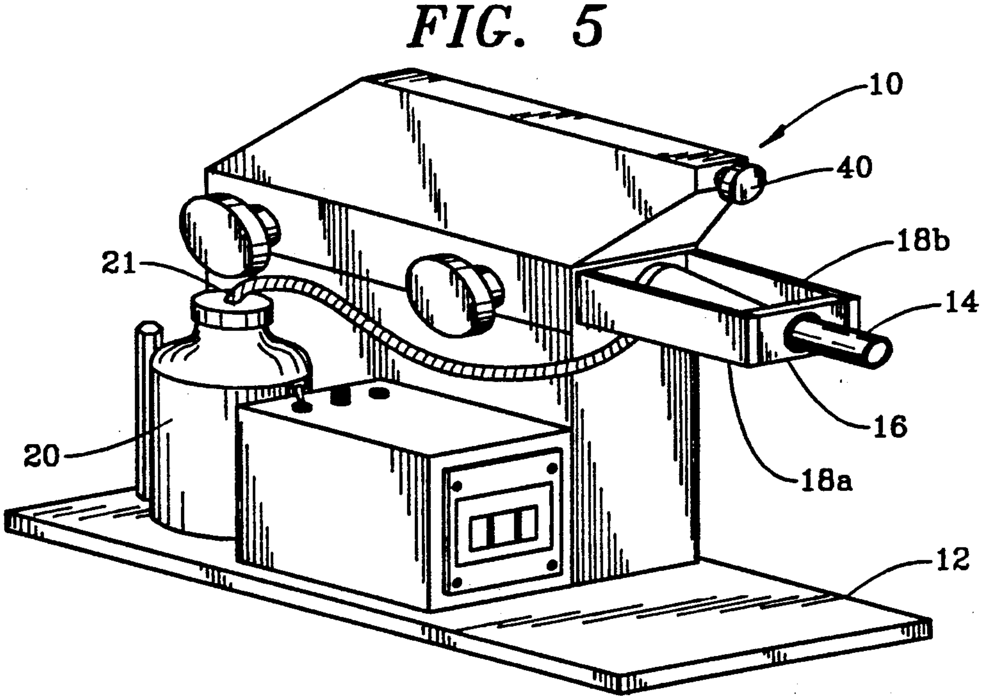
FIG. 5 shows an isometric view of apparatus embodying the components shown in FIGS. 1-4.

Referring now to the accompanying drawings, a portable injection unit 10 (FIG. 5) has a base plate 12 adapted to rest on a fixed support (not shown). A rigid tube 14 extends horizontally from the upper part of the unit. One end of the tube is enlarged and screwed into an opening through a cross bar 16. The bar 16 is fastened between the projecting ends of a pair of brackets **18*a* and 18*b* integral with an upper cross plate 18C (FIGS. 7-9) held in unit 10**.

A container 20 holds a supply of fluid vaccine or the like, and is secured to base plate 12. A conduit 21 supplies dosage (e.g., subcutaneous oil-base vaccine) from container 20 to a pump unit 22 and thence through an injection needle 24 carried at one end of pump 22. An electric motor 26 (FIG. 9) advances and retracts pump unit 22 and needle 24. Pump 22 has internal means for causing the pump to be primed with a measured amount of fluid dosage while it is retracted, and to eject the measured dosage when the needle reaches its most advanced position, as disclosed in U.S. Pat. Nos. 4,838,866 of Marshall, issued Jun. 13, 1989, and 4,758,227 of Lancaster et al., issued Jul. 19, 1988.

Figure 7:
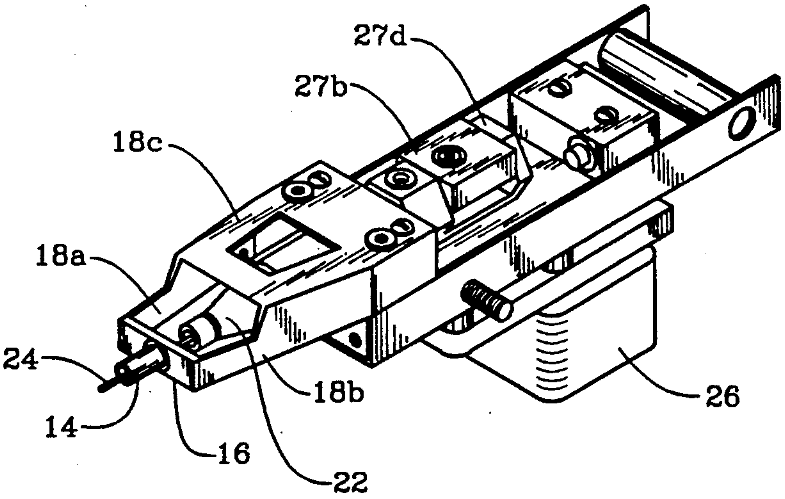
FIG. 7 shows an isometric view, in reduced scale, of parts of the apparatus shown in FIG. 6 for advancing and retracting the needle and pump shown in FIGS. 1-4, in retracted position.
Figure 8:
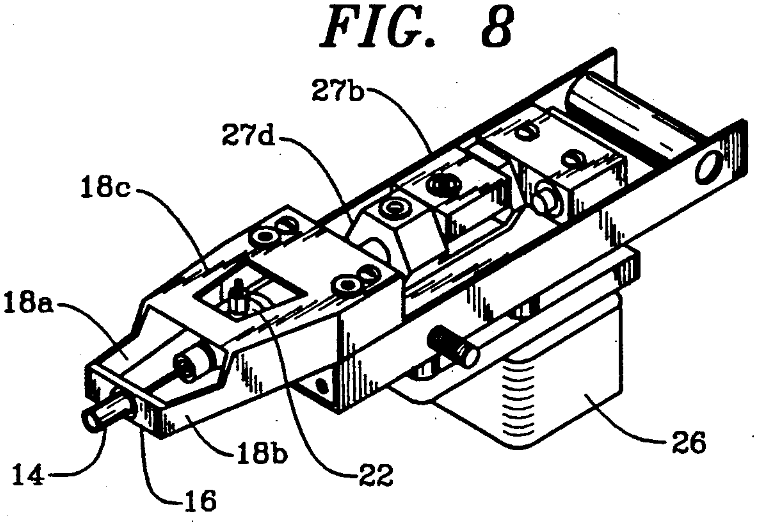
FIG. 8 corresponds to FIG. 7, but shows the needle and pump in advanced position for injection.
Figure 9:
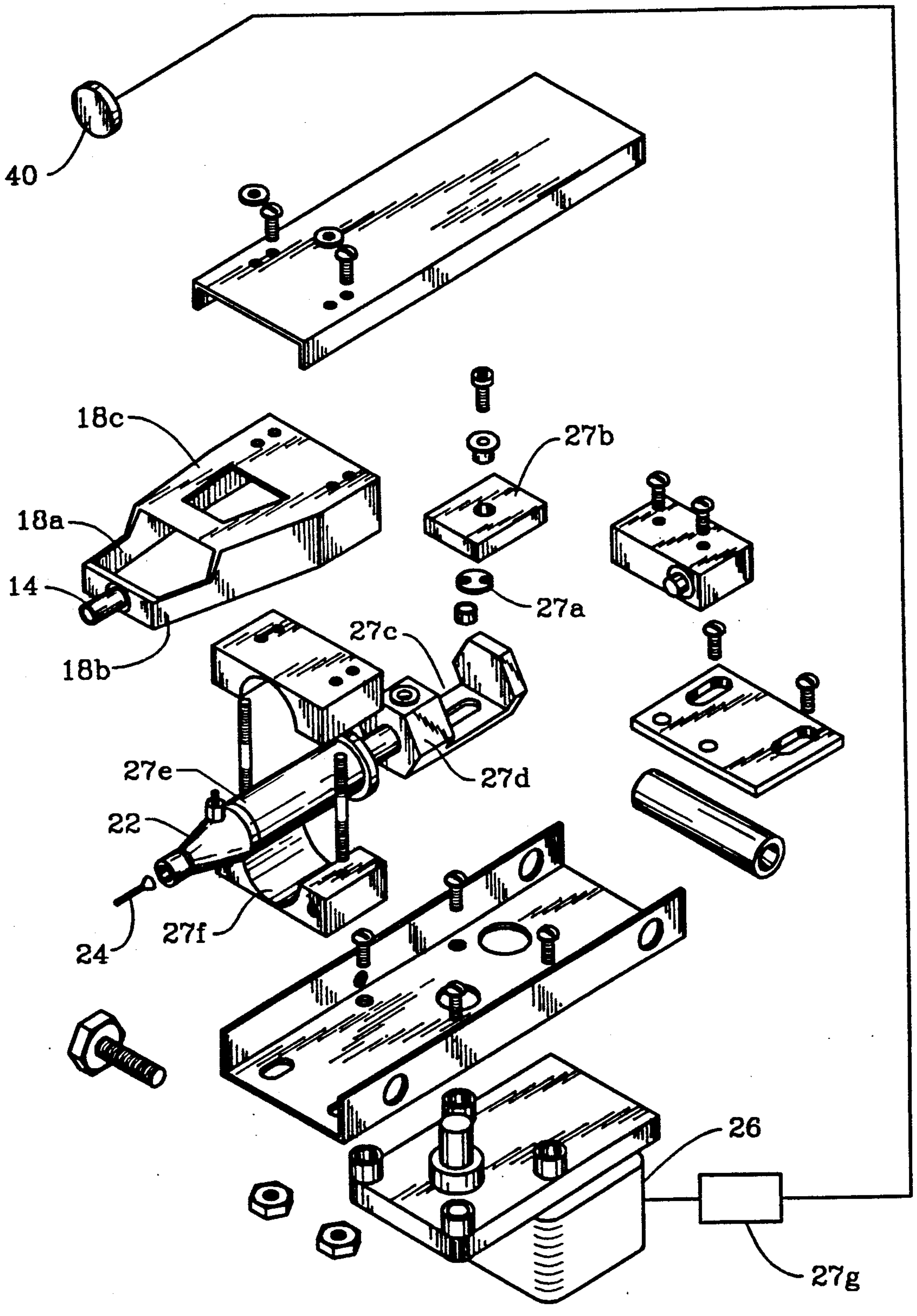
FIG. 9 shows an exploded view, in further reduced scale, of the parts shown in FIGS. 7 and 8, with related parts.

Pump 22 is driven by motor 26 by the means shown in FIGS. 7-9, using essentially the drive means and controls for operating an injection pump disclosed in the said U.S. Pat. No. 4,758,227. The motor 26 turns as eccentric **27*a* to cause a block 27*b*, which fits in a slot 27*c* in a member 27*d*, to reciprocate the member 27*d* and thus pump 22. The rear end of pump 22 is attached to member 27*d*, and a cylindrical case 27*e* around pump 22 is slidable through a split bearing 27*f* to cause pump 22 and needle 24 to reciprocate in the direction hereinafter described. A circuit 27*g* connected to button 40 and motor 26** controls operation of the motor.

The end of pump 22 which carries needle 24 is tapered and moves into the opening 15 through the enlarged end of tube 14 when the sharp end 24' of needle 24 reaches the limit of its movement beyond the projecting end of tube 14. When pump 22 and needle 24 are fully retracted, the sharp needle end 24' is enclosed within tube 14, so that fingers of an operator of unit 10 are protected against touching the sharp needle end 24' while the needle is in its retracted position.

The thumb 31' and forefinger of a person's hand 31 may be used to draw a fold of skin 30 from the neck 32 of a chicken 34 over the top and sides of the projecting end of tube 14. This causes a part 30*a* of the bird's skin to extend closely across the projecting end of tube 14, while another part 30*b* of the skin slopes down at a divergent angle from the end of tube 14 and away from skin part 30*a*. The result is a cavity 36 bounded by skin parts 30*a* and 30*b* and the underlying firm muscle tissue 38 of the bird's neck 32. The space within cavity 36 is filled with loose fatty tissue which can safely receive an injection of vaccine from needle 24 (typically about half cc).

The needle point 24' in its advanced position is preferably offset downwardly from the central axis from the projecting end of tube 14, far enough to point toward where skin part 30*b* approaches convergence with the underlying muscle tissue 38. In order to achieve this position of needle point 24', it is desirable to slope the needle and its line of movement slightly downwardly relative to the central axis to tube 14 toward the projecting end of tube 14, while still keeping the furthest advance of needle point 24' spaced above solid tissue 38 and away from skin part 30*b*. For example, the projecting end of tube 14 may have an inner radius of 0.312 inch, an outer radius of 0.375 inch, a length of 0.325 inch beyond the retracted tip of the needle, and a slope of 6.3 degrees of its central axis relative to the position may project $\frac{3}{8}$ inch beyond the projecting end of tube 14, ending where it would touch the inside of tube 14 if the tube extended that far.

A spring-loaded control button 40 projects in the same direction as tube 14 but at a higher level and further back than the projecting end of tube 14, in order to position the button where it can be pressed by the knuckles of a hand whose thumb and forefinger are at the same time pressing against a bird's skin being held against the sides of tube 14. Button 40 is centered vertically above tube 14 to facilitate operation of the unit 10 by anyone who is either right handed or left handed. The button is connected to circuits for controlling advance and retracting of needle 24 and for controlling operation of pump 22. When the button is pressed, the pump and needle are advanced, at the end of the advance the pump is caused to inject one measured dose through the needle, and then the pump and needle are retracted to their starting positions ready to repeat the cycle when the button is pressed again.

Figure 6:
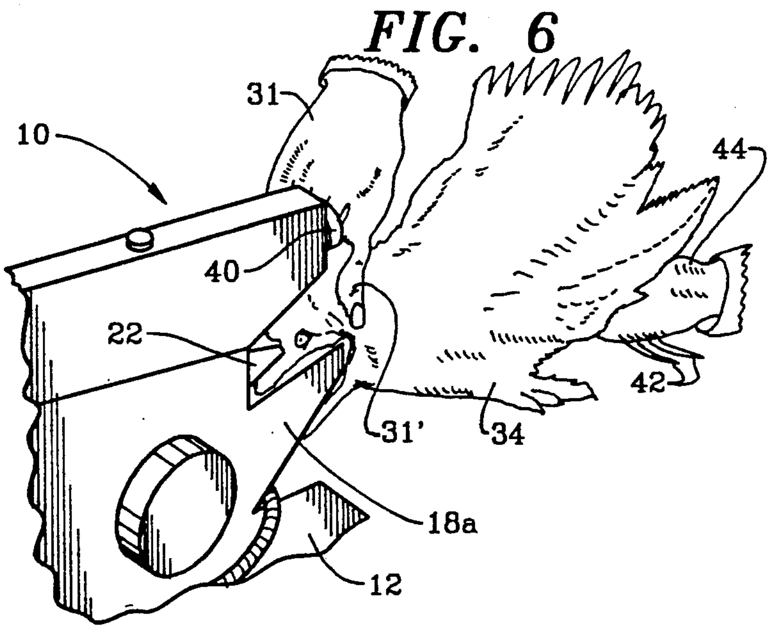
FIG. 6 shows a perspective view of a chicken being injected by the means shown in FIG. 1-5.

A single person may inject a chicken 34 in unit 10 (FIG. 6) by facing the projecting end of tube 14, grasping the legs (which include feet 42) of the chicken with the left hand 44 to support and control the body of the chicken, and using the right hand 31 to pinch loose skin 30 on the upper part of the chicken's neck 32, about half way along the length of the neck, and to draw the skin upwardly from the neck across the projecting end of tube 14 and then far enough along the top of tube 14 to permit the thumb 31' and forefinger 31'' of hand 31 to press some of the drawn skin against the sides of tube 14. Meanwhile, upward pull on skin 30 pulls up the chicken's neck until part of the neck engages the bottom of the outer end of tube 14, thus lining up that part of the neck with the length of tube 14, while the extension of the neck toward the head of the chicken is held down by cross bar 16. The thumb 31' and forefinger 31'' of hand 31 continue pressure along the sides of tube 14 while moving just enough to roll the knuckle of the hand 31 to press against button 40. This causes pump unit 22 and needle 24 to advance until the pointed needle point 24' pierces skin part 30*a* and stops within cavity 36. The pump 22 then automatically causes needle 24 to eject a measured dose of vaccine immediately after the pump and needle have moved to their fully advanced positions. They are automatically retracted to their starting positions after ejection, and the injected chicken is released. Tests have shown that a single person can inject about 475 chickens in a one hour period with no more than one per cent of the chickens failing to receive the intended injection.

While present preferred embodiments and practices of the invention have been illustrated and described, it may be otherwise variously embodied and practiced within the scope of the following claims.

We claim:

1. Apparatus for injecting a fluid dose through loose skin around a bird's neck, comprising a needle having a sharp end, a passage extending lengthwise through the needle, an outlet from the passage adjacent said sharp end and an inlet into the passage adjacent the other end of the needle, means to supply a fluid dose to said inlet, a structure supporting the needle, said structure having a portion extending around the needle and elongated toward one end of said portion, said elongated portion of the structure having a first exterior surface engageable with a bird's neck extending in the direction of elongation of said portion of the structure, and having a second exterior surface on a substantially opposite side of said portion of the structure, said exterior surfaces being spaced apart sufficiently for a fold of loose skin on a neck so engaged by the first exterior surface to be drawn across said end of said portion and over said second exterior surface, and means mounting the needle for lengthwise movement from a retracted position in which its sharp end is covered by said portion of the structure to an extended position in which said sharp end projects beyond said end of the said portion, said lengthwise movement of the needle being in a path which passes between said exterior surfaces closer to the first surface than to the second surface, and also extends in a lien which converges toward said first exterior surface as it progresses toward the extended position of the needle.

2. Apparatus according to claim 1, in which said elongated portion of the structure has a cylindrical interior surface concentric with said path of the needle, the sharp end of the needle in its extended position being substantially coincident with a projection of said cylindrical interior surface.

* * * * *